United States Patent [19]

Chen

[11] Patent Number: 5,047,063
[45] Date of Patent: Sep. 10, 1991

[54] ADJUSTMENT DEVICE FOR ARTIFICIAL LIMBS

[76] Inventor: Sen-Jung Chen, No. 236, Sec. 3, Ho-Ping West Road, Taipei, Taiwan

[21] Appl. No.: 620,203

[22] Filed: Nov. 30, 1990

[51] Int. Cl.$^5$ .............................................. A61F 2/62
[52] U.S. Cl. ...................................... 623/38; 623/27; 403/59
[58] Field of Search ............... 623/38, 39, 27; 403/59, 403/90, 113, 135, 362

[56] References Cited

U.S. PATENT DOCUMENTS

| 4,608,054 | 8/1986 | Schröder | 623/39 |
| 4,676,800 | 6/1987 | Chen | 623/38 |

FOREIGN PATENT DOCUMENTS

| 1054398 | 4/1959 | Fed. Rep. of Germany | 403/135 |
| 1502061 | 11/1967 | France | 623/38 |
| 0638095 | 9/1983 | Switzerland | 623/38 |
| 0721094 | 3/1980 | U.S.S.R. | 623/38 |
| 1026803 | 7/1983 | U.S.S.R. | 623/38 |
| 8706819 | 11/1987 | World Int. Prop. O. | 623/39 |

Primary Examiner—Randall L. Green
Assistant Examiner—David H. Willse
Attorney, Agent, or Firm—Cushman, Darby & Cushman

[57] ABSTRACT

An adjustment device for artificial limbs includes a hollow cylindrical member having an open upper section and an open bottom end, and a plate member disposed on and covering the open bottom end. A coupling member is received in the hollow cylindrical member and has a top plate portion to cover a central through opening of the plate member, and a downwardly extending post portion projecting from the top plate portion and having a diameter smaller than the central through opening. The post portion extends through the central through opening of the plate member. The hollow cylindrical member is laterally movable to adjust the position of the post portion in the central through opening. The post portion extends into a sleeve member. A mounting member has a cylindrical portion with an upper surface which is provided with a concave recess. The sleeve member is tiltably received in the concave recess so as to guide the post portion in an inclined position relative to a vertical axis of the mounting member. The lateral position of the post portion in the through opening and the inclination of the post portion relative to the vertical axis of the mounting member is adjusted to correspondingly adjust the center of gravity of an artificial limb incorporating the adjustment device to match the body equilibrium of a user.

4 Claims, 6 Drawing Sheets

ADJUSTMENT DEVICE FOR ARTIFICIAL LIMBS

BACKGROUND OF THE INVENTION

1. Field Of The Invention

The invention relates to an adjustment device for artificial limbs, more particularly to an adjustment device by which the gravitational equilibrium of an artificial limb incorporating the device can be easily adjusted.

2. Description Of The Related Art

Although many improvements have been made in the construction of artificial limbs, there is still much room left for improvement, particularly in the construction of joints for artificial knees and ankles so as to suit the joints to the wearer's body dimensions and walking conditions. Generally, the upper and/or lower portions of artificial joints are provided with an adjustment device. Referring to FIG. 1, an adjustment device for an artificial limb, as disclosed in U.S. Pat. No. 4,676,800 of the applicant, is shown to comprise a coupling member A to be connected to an upper joint portion of an artificial limb and having a circular joint projection a1 on a top end. A cylindrical member B has an open section at an upper end to fixedly couple the same with a lower portion of an artificial limb. The cylindrical member B further includes a lower end having an annular recess b1 provided with a plurality of cavities and through openings formed therein. Screw bolts C are received in the cavities of the cylindrical member B and extend into the annular recess b1 through the through openings to couple the cylindrical member B with the joint projection a1 of the coupling member A. By adjusting the screw bolts C, the cylindrical member B can be tilted relative to the coupling member A so as to easily adjust the center of gravity or the gravitational equilibrium of an artificial limb incorporating the device.

One of the disadvantages of this conventional adjustment device is that adjustment of the gravitational equilibrium is achieved only by varying the angle of tilt of the cylindrical member B relative to the coupling member A. Thus, simple lateral adjustment of the position of the cylindrical member B relative to the coupling member A is not possible.

SUMMARY OF THE INVENTION

Therefore, the objective of the present invention is to provide an improved adjustment device for artificial limbs that overcomes the problems associated with the prior art.

Accordingly, a preferred embodiment of an adjustment device for artificial limbs of the present invention comprises a hollow cylindrical member having an open upper section and an open bottom end, and a plate member disposed on and covering the open bottom end. A coupling member is received in the hollow cylindrical member and has a top plate portion to cover a central through opening of the plate member, and a downwardly extending post portion projecting from the top plate portion and having a diameter smaller than the central through opening. The post portion extends through the central through opening of the plate member. The hollow cylindrical member is laterally moved to adjust the position of the post portion in the central through opening. The post portion extends into a sleeve member having an annular plate portion abutting a bottom surface of the plate member, and a hollow guide portion extending downward from the annular plate portion and having a downwardly tapered convex surface. A mounting member has a cylindrical portion with an upper surface provided with a concave recess. The hollow guide portion of the sleeve member is tiltably received in the concave recess so as to guide the post portion in an inclined position relative to a vertical axis of the mounting member. The adjustment device further comprises a first adjusting and locking means to adjustably lock the post portion against the hollow cylindrical member in the desired lateral position, and a second adjusting and locking means to adjustably lock the post portion against the mounting member in the desired inclined position. The first adjusting and locking means prevents rotation of the hollow cylindrical member relative to the post portion. Of the hollow cylindrical member and the mounting member, one is adapted for connection with an artificial limb joint, and the other is adapted for connection with an artificial limb. The lateral position of the post portion in the through opening and the inclination of the post portion relative to the vertical axis of the mounting member is adjusted to correspondingly adjust the center of gravity of the artificial limb incorporating the adjustment device to match the body equilibrium of a user.

The plate member has a plurality of radially extending threaded bores communicated with the central through opening. The post portion has a serrated periphery adjacent to the threaded bores. The first adjusting and locking means includes a plurality of elongated fasteners threadedly disposed in the radial threaded bores and having ends extending into the central through opening and engaging the serrated periphery.

The hollow guide portion is divided into a plurality of spaced claw-like members. The cylindrical portion of the mounting member is provided with a plurality of inwardly projecting radial protrusions. Each radial protrusion extends into and between two adjacent claw-like members and is provided with a threaded hole. The post portion has a plurality of cavities below the serrated periphery to be respectively aligned with the radial protrusions. The second adjusting and locking means, like the first adjusting and locking means, includes a plurality of elongated fastening members. Each fastening member is threadedly disposed in the threaded hole of one radial protrusion and has one end extending toward the cavities. One end of each second elongated fastener bears against the post portion at one of the cavities thereof.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
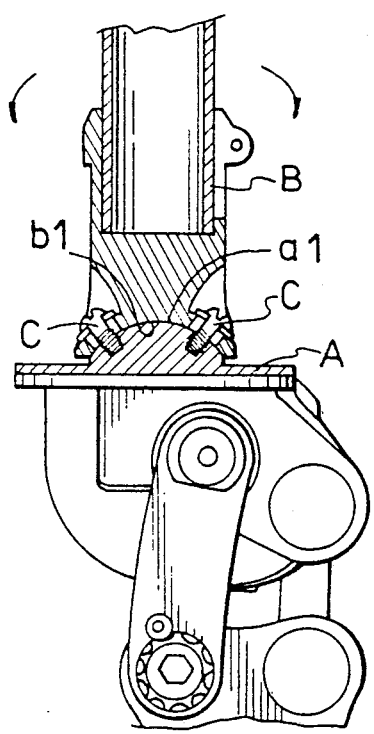
FIG. 1 is a sectional view of a conventional adjustment device for artificial limbs disclosed in U.S. Pat. No. 4,676,800 of the applicant.
Figure 2:
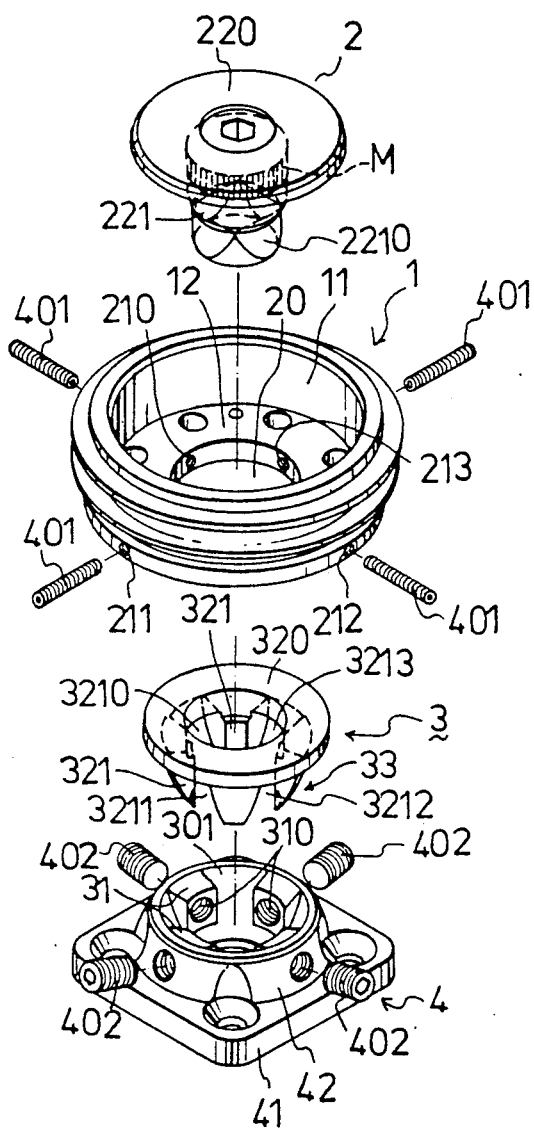
FIG. 2 is an exploded view of a first preferred embodiment of an adjustment device for artificial limbs according to the present invention.
Figure 3:
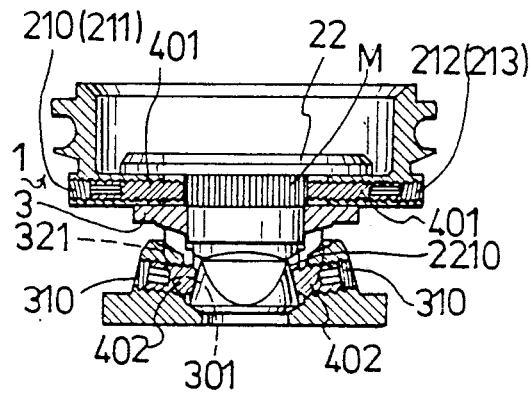
FIG. 3 is a sectional view illustrating the assembly of the adjustment device shown in FIG. 2.

Referring to FIGS. 2 and 3, the first preferred embodiment of an adjustment device for artificial limbs according to the present invention is shown to comprise a hollow cylindrical member 1, a coupling member 2, a sleeve member 3, a mounting member 4 and fastening means 401 and 402.

The hollow cylindrical member 1 has an open upper section 11 and a plate member 12 disposed on and covering the open bottom end of the cylindrical member 1. The plate member 12 has a circular through opening 20 and four radially extending spaced threaded bores 210, 211, 212, and 213 communicated with the through opening 20. The upper portion of the cylindrical member 1 is adapted for connection to a tubular end of an artificial limb. The lower portion of the cylindrical member 1 is adapted for connection with an artificial limb joint or with another artificial limb.

The coupling member 2 is received in the cylindrical member 1 and has a circular plate portion 220 to cover the through opening 20. The coupling member 2 further has a downwardly extending post 221 projecting from the plate portion 220 and extending through the through opening 20 of the plate member 12. The diameter of the post 221 is smaller than that of the through opening 20. The post 221 has a serrated periphery M provided adjacent to the threaded bores 210, 211, 212, and 213.

The post 221 extends into the sleeve member 3. The sleeve member 3 has an annular plate portion 320 abutting the bottom surface of the plate member 12, and a hollow guide portion 33 extending downward from the annular plate portion 320 and having a downwardly tapered convex surface. The guide portion 33 is divided into four spaced claw-like members 321.

The mounting member 4 has a rectangular mounting pad 41 and an upwardly protruding cylindrical portion 42 projecting from the mounting pad 41. The upper surface of the cylindrical portion 42 is provided with a hemispherical recess 301. The cylindrical portion 42 is further provided with equally spaced radial inward projections 31 protruding into the recess 301. Each of the inward projections 31 has a downwardly inclining threaded through bore 310. The guide portion 33 is tiltably fitted into the recess 301 so as to guide the post 221 in an inclined position relative to the vertical axis of the mounting member 4. When fitted, the inward projections 31 extend between notches 3210, 3211, 3212, and 3213 which are respectively formed between two consecutive claw-like members 321. Rotation of the sleeve member 3 relative to the mounting member 4 is thus prevented.

The post 221 has four substantially V-shaped cavities 2210 disposed below the serrated periphery M and having a downwardly and outwardly inclining bearing face. The cavities 2210 are to be aligned with the through bore 310 of one of the inward projections 31.

The fastening means 4 includes a first and a second set of fastening members 401 and 402. The fastening members 401 are threadedly disposed in the threaded bores 210, 211, 212, and 213 and have ends extending into the central through opening 20 of the plate member 12 and engaging the serrated periphery M of the post 221. The cylindrical member 1 is laterally moved to change the position of the post 221 in the through opening 20. The fastening members 401 are provided to adjustably lock the post 221 against the cylindrical member 1 in the desired lateral position. The fastening members 401 also prevent the rotation of the cylindrical member 1 relative to the post 221.

The fastening members 402 are threadedly received in the threaded bores 310 of the mounting member 4 and have one end extending toward the cavities 2210 of the post 221. The threaded bores 310 guide the fastening members 402 so as to properly bear against the post 221 at the bearing faces of the cavities 2210. The fastening members 402 are used to adjustably lock the position of the post 221 in the recess 301.

Figure 4A:
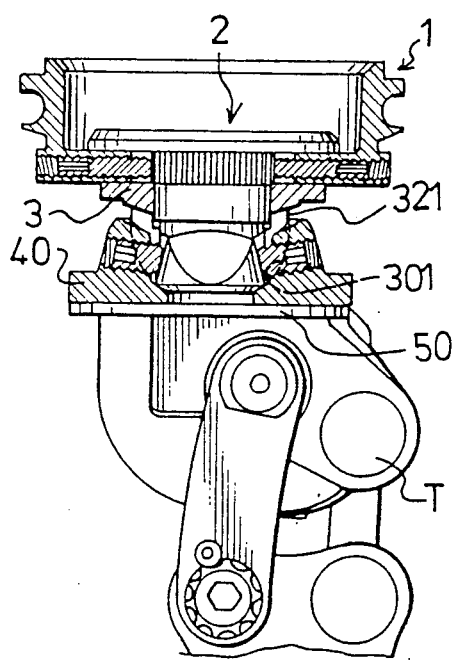
FIGS. 4A and 4B illustrate the adjustment of the first preferred embodiment to match the center of gravity of an artificial limb incorporating the device with the body equilibrium of a user.
Figure 4B:
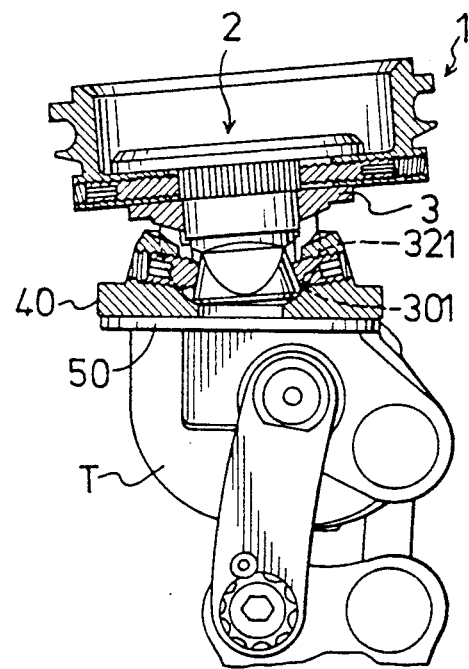

The mounting member 4 of the assembled first preferred embodiment is to be connected to an upper seat portion 50 of an artificial limb joint T, such as a knee joint. Referring to FIG. 4A, the position of the cylindrical member 1 relative to the coupling member 2 can be adjusted by simply loosening the fastening members 401, moving the cylindrical member 1 in a lateral direction to a desired position relative to the coupling member 2, then re-tightening the fastening members 401. Referring to FIG. 4B, the inclination of the cylindrical member 1 can be varied by adjusting the position of the post 221 in the recess 301. The position of the post 221 on the recess 301 can be adjusted by simply loosening the fastening members 402, tilting the post 221 along the recess 301 to the desired inclination, then re-tightening the fastening members 402. By adjusting the lateral position and the inclination of the cylindrical member 1, the center of gravity of an artificial limb incorporating the first preferred embodiment can be adjusted to match the body equilibrium of the user.

Figure 5:
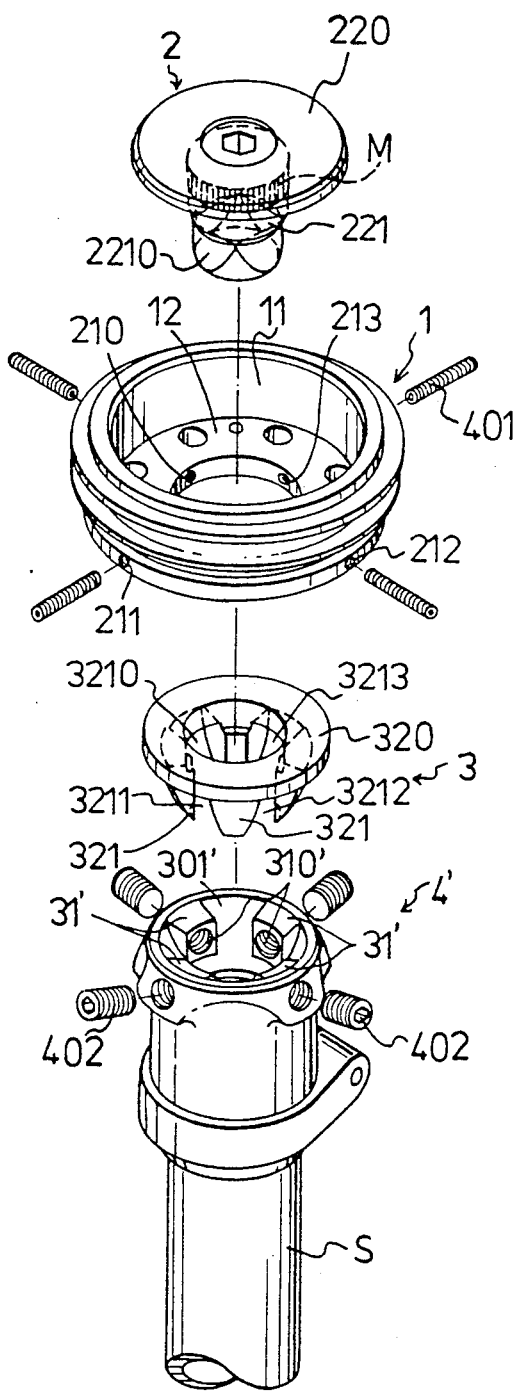
FIG. 5 is an exploded view of a second preferred embodiment of an adjustment device for artificial limbs according to the present invention.

An exploded view of the second preferred embodiment of an adjustment device according to the present invention is shown in FIG. 5. The second preferred embodiment is substantially similar to the first preferred embodiment, the difference residing in the construction of the mounting member 4'. While the mounting member 4 of the first preferred embodiment is adapted to be connected to an artificial limb joint, the mounting member 4' of the second preferred embodiment is adapted to be directly connected to a portion S of an artificial limb.

Figure 6:
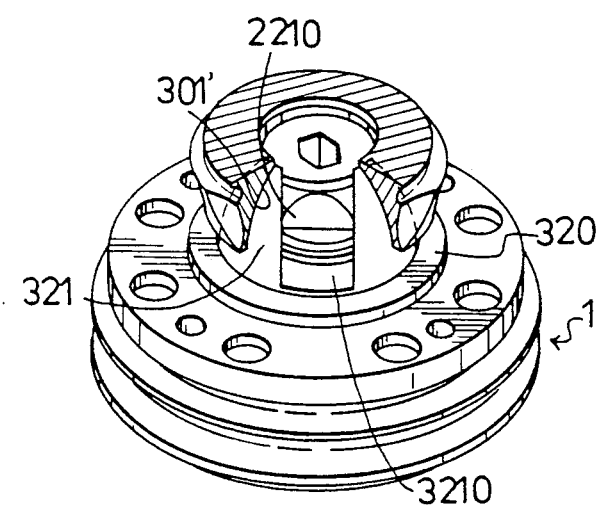
FIG. 6 is an inverted, partly sectional view of the second preferred embodiment to illustrate its assembly.

The mounting member 4' is a cylindrical member having an upper end provided with a hemispherical recess 301'. The mounting member 4' is also provided with equally spaced radial inward projections 31' protruding into the recess 301' and having a downwardly inclining threaded through bore 310'. An inverted, partly sectional view of the second preferred embodiment is shown in FIG. 6. When the sleeve member 3 is fitted into the recess 301', the inward projections 31' similarly extend into and between the notches 3210, 3211, 3212, and 3213. Thus, rotation of the sleeve member 3 relative to the mounting member 4 is prevented.

Figure 7A:
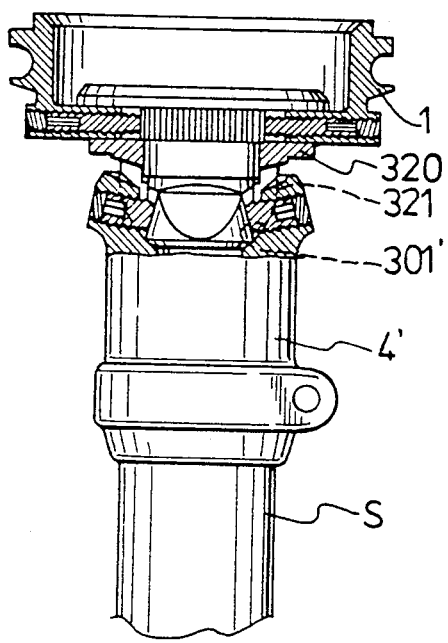
FIGS. 7A and 7B illustrate the adjustment of the second preferred embodiment to match the center of gravity of an artificial limb incorporating the second preferred embodiment with the body equilibrium of a user.
Figure 7B:
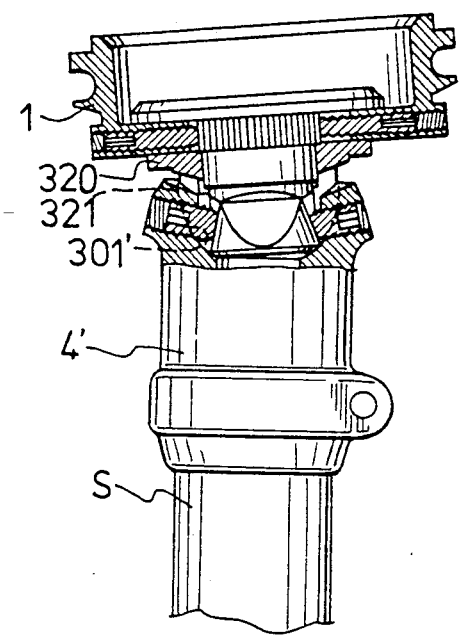

FIGS. 7A and 7B illustrate the adjustment of the lateral position and the inclination of the cylindrical member 1 of the second preferred embodiment to match the center of gravity of an artificial limb incorporating the second preferred embodiment with the body equilibrium of the user. Since the construction of the second preferred embodiment is similar to that of the first preferred embodiment, its operation is similar and as such, will not be detailed.

While the present invention has been described in connection with what is considered the most practical and preferred embodiments, it is understood that this invention is not limited to the disclosed embodiments, but is intended to cover various arrangements included within the spirit and scope of the broadest interpretation so as to encompass all such modifications and equivalent arrangements.

I claim:

1. An adjustment device for artificial limbs, comprising:
  a hollow cylindrical member having an open upper section and an open bottom end;
  a plate member disposed on and covering said open bottom end, said plate member having a central through opening;
  a coupling member received in said hollow cylindrical member, said coupling member having a top plate portion to cover said central through opening, and a downwardly extending post portion projecting from said top plate portion and having a diameter smaller than said central through opening, said post portion extending through said central through opening of said plate member, said hollow cylindrical member being laterally movable to adjust the position of said post portion in said central through opening;
  a sleeve member having an annular plate portion abutting the bottom surface of said plate member, and a hollow guide portion extending downward from said annular plate portion, said hollow guide portion having a downwardly tapered convex surface, said post portion extending into said sleeve member;
  a mounting member having a cylindrical portion with an upper surface provided with a concave recess, said hollow guide portion being tiltably received in said concave recess so as to guide said post portion in an inclined position relative to a vertical axis of said mounting member;
  a first adjusting and locking means to adjustably lock said post portion against said hollow cylindrical member in the desired lateral position, said first adjusting and locking means preventing the rotation of said hollow cylindrical member relative to said post portion; and
  a second adjusting and locking means to adjustably lock said post portion against said mounting member in the desired inclined position;
  one of said hollow cylindrical member and said mounting member being adapted for connection with an artificial limb joint; the other of said hollow cylindrical member and said mounting member being adapted for connection with an artificial limb;
  whereby, the lateral position of said post portion in said through opening and the inclination of said post portion relative to the vertical axis of said mounting member can be adjusted to correspondingly adjust the center of gravity of the artificial limb incorporating said adjustment device to match the body equilibrium of a user.

2. The adjustment device as claimed in claim 1, wherein said plate member has a plurality of radially extending threaded bores communicated with said central through opening, said post portion having a serrated periphery adjacent said threaded bores, said first adjusting and locking means including a plurality of first elongated fasteners threadedly disposed in said radial threaded bores and having ends extending into said central through opening and engaging said serrated periphery.

3. The adjustment device as claimed in claim 2, wherein said hollow guide portion is divided into a plurality of spaced claw-like members, said cylindrical portion of said mounting member being provided with a plurality of inwardly projecting radial protrusions, each said radial protrusion extending into and between two adjacent said claw-like members and having a threaded hole, said post portion having a plurality of cavities below said serrated periphery to be respectively aligned with said radial protrusions, said second adjusting and locking means including a plurality of second elongated fasteners, each said second elongated fastener being threadedly disposed in said threaded hole of one said radial protrusion and having one end extending toward said cavities, one end of each said second elongated fastener bearing against said post portion at one of said cavities.

4. The adjustment device as claimed in claim 3, wherein said post portion has downwardly and outwardly inclining bearing faces at said cavities, said second threaded bores having inner ends which are inclined downward so as to guide said second elongated fasteners to properly bear against said bearing faces.

* * * * *